United States Patent [19]

Wattimena

[11] 4,086,282

[45] Apr. 25, 1978

[54] PROCESS FOR PREPARATION OF 3,5-XYLENOL

[75] Inventor: Freddy Wattimena, Amsterdam, Netherlands

[73] Assignee: Shell Oil Company, Houston, Tex.

[21] Appl. No.: 681,358

[22] Filed: Apr. 29, 1976

[51] Int. Cl.² ............................................. C07C 37/06
[52] U.S. Cl. .............................................. 260/621 H
[58] Field of Search ...................... 260/621 R, 621 H

[56] References Cited

U.S. PATENT DOCUMENTS

| | | |
|---|---|---|
| 2,369,197 | 2/1945 | Winkler ........................... 260/621 R |
| 2,413,598 | 12/1946 | Ballard et al. ................... 260/621 R |
| 3,959,392 | 5/1976 | Szcepanski et al. ............. 260/621 H |

*Primary Examiner*—Bernard Helfin
*Assistant Examiner*—Werren B. Lone

[57] ABSTRACT

3,5-Xylenol is prepared in high yield from isophorone by heating isophorone at a temperature of from about 450° to about 650° in the presence of a halogen having an atomic number of at least 17 or an organic compound containing such a halogen.

7 Claims, No Drawings

PROCESS FOR PREPARATION OF 3,5-XYLENOL

BACKGROUND OF THE INVENTION

This invention relates of a process for the preparation of 3,5-xylenol from 3,5,5-trimethylcyclohexen-2-one (isophorone). 3,5-Xylenol and related xylenol isomers are useful as disinfectants and starting materials for the preparation of resins.

It is known from U.S. Pat. No. 2,369,196 that isophorone can be converted to 3,5-xylenol by heating isophorone at temperatures between 668° and 676° C. The yields of product, however, are relatively low (39%). It is also known to use a variety of solid catalysts to improve the yield. Examples of such catalysts are activated alumina disclosed in U.S. Pat. No. 2,369,197 and a chromium (III) oxide-copper (I) oxide mixture known from British Patent specification No. 1,197,803. A disadvantage of such solid catalysts is that during the conversion reaction a carbon deposit is formed on the catalyst. This leads to a decrease in catalyst activity and necessitates stopping the reaction at intervals in order to regenerate the catalyst.

It has now been found that isophorone can be converted to 3,5-xylenol in good yield using certain homogeneous catalysts.

SUMMARY OF INVENTION

The present invention, therefore, relates to an improved process for the preparation of 3,5-xylenol which comprises heating isophorone at a temperature of from about 450° to about 650° C in the presence of a homogeneous catalyst comprising a halogen having an atomic number of at least 17 or an organic compound containing said halogen, said organic compound being selected from the class consisting of halogen substituted-saturated aliphatic, unsaturated aliphatic and aromatic compounds.

DESCRIPTION OF THE PREFERRED EMBODIMENTS

The halogen catalyst for the process of the invention, in molecular form, may be chlorine, bromine or iodine. The halogen substituted, organic compound catalyst of the invention may contain any of these three halogens, but is preferably an iodine-containing compound. The halogen-containing organic compound may be a saturated or unsaturated aliphatic compound or an aromatic compound. The aliphatic compound preferably contains from 1 to 6 carbon atoms, and may be for example, a haloalkane such as methyl iodide, n-butyl bromide or carbon tetrachloride, or an allyl halide such as allyl bromide. The aromatic compound may be a phenyl halide such as phenyl iodide. The amount of catalyst may be from 0.01 to 20%w, and is preferably from 0.1 to 5.0%w based on the weight of isophorone.

The process is preferably carried out at a temperature of 550° to 650° C. The pressure is conveniently atmospheric pressure, although the process may also be carried out at sub-atmospheric or super-atmospheric pressures.

In one embodiment the process is carried out continuously by passing the isophorone and the catalyst through a heated tube reactor. The isophorone and the catalyst may also be mixed with an inert diluent, for example nitrogen or an alkane, in order to improve the selectivity of the process and/or the heat transfer in the reactor. In some circumstances it may also be advantageous to irradiate the reaction mixture with ultra-violet radiation.

The 3,5-xylenol may be recovered from the reaction mixture and purified by any suitable method, for example by distillation. From the economic point of view it may also be desirable to include in the process a separate recovery step for the halogen or halogen-containing organic compound.

The invention is illustrated further in the following Examples.

EXAMPLES 1 TO 12

To evaluate the effectiveness of the homogeneous catalysts of the invention, a series of tests were performed in a heated tubular reaction vessel wherein isophorone was converted to 3,5-xylenol with different halogen-containing catalysts according to the invention at varying catalyst concentrations, reactant space velocities and temperatures.

The reactor consisted of a stainless steel tube of length 320 mm and diameter 10 mm fitted with a thermocouple of diameter 5 mm along its whole length. The tube was surrounded by an electrically heated oven. The catalyst was dissolved in isophorone and the mixture was passed at a constant space velocity through the heated tube. The product was dissolved in acetone and analysed by gas-liquid chromatography.

The results of the various examples as well as further details of the operating procedures are set out in the Table below.

The yields of product from a number of experiments were combined (total 548.6 g) and distilled under reduced pressure. 3,5-Xylenol having a purity of more than 99% was obtained in 85.4% yield, b.p. 90°–95° C at 1 mm Hg.

TABLE

| Example | Catalyst | Catalyst Concentration (%w based on Isophorone) | Temperature (° C) | Space Velocity (ml.ml Reactor,hr) | Conversion Isophorone (%) | Selectivity to 3,5-Xylenol (%) |
| --- | --- | --- | --- | --- | --- | --- |
| 1 | methyl iodide | 0.1 | 600 | 0.33 | 93.9 | 79.9 |
| 2 | " | 0.5 | 600 | 0.33 | 97.6 | 83.2 |
| 3 | " | 1.0 | 475 | 0.33 | 30 | 94 |
| 4 | " | 1.0 | 570 | 0.5 | 100 | 85 |
| 5 | " | 1.5 | 570 | 0.5 | 100 | 93 |
| 6 | " | 5.0$^a$ | 570 | 0.5 | 100 | 95 |
| 7 | " | 10.0 | 550 | 0.66 | 100 | 85 |
| 8 | n-butyl bromide | 1.0 | 600 | 0.33 | 94.8 | 80.4 |
| 9 | carbon tetrachloride | 1.0 | 600 | 0.33 | 96 | 65 |
| 10 | allyl bromide | 1.2 | 570 | 0.8 | 75 | 81 |
| 11 | phenyl iodide | 1.3 | 570 | 0.3 | 99 | 86 |
| 12 | bromine$^b$ | 2.4 | 570 | 0.6 | 76 | 84 |

TABLE-continued

| Example | Catalyst | Catalyst Concentration (%w based on Isophorone) | Temperature (° C) | Space Velocity (ml.ml Reactor,hr) | Conversion Isophorone (%) | Selectivity to 3,5-Xylenol (%) |
|---|---|---|---|---|---|---|
| Comparative | none | — | 600 | 0.023 | 70 | 50 |

<sup>a</sup>Reaction mixture was diluted with nitrogen; molar ratio N$_2$: isophorone = 1 : 4.
<sup>b</sup>Used as solution in benzene (9.3 g Br$_2$ per 100 ml C$_6$H$_6$).

What is claimed is:

1. A process for the preparation of 3,5-xylenol from isophorone which comprises heating isophorone at a temperature of from about 450° to about 650° C in the presence of a homogeneous catalyst selected from the class consisting of a halogen having an atomic number of at least 17 and an organic compound containing said halogen, said halogen being selected from the class consisting of molecular chlorine, bromine and iodine and said organic compound being selected from the class consisting of haloalkanes of 1 to 6 carbon atoms allyl halides and phenyl halides.

2. The process according to claim 1, wherein the catalyst is a phenyl halide.

3. The process according to claim 1, wherein the catalyst is an iodine-containing compound.

4. The process according to claim 2, wherein the catalyst is phenyl iodide.

5. The process according to claim 5, wherein the catalyst is methyl iodide.

6. The process according to claim 1, wherein the amount of catalyst used is from 0.1 to 5% by weight based on the weight of isophorone.

7. The process according to claim 6 wherein the temperature is from 550° to 650° C.

* * * * *